United States Patent [19]

Giese

[11] Patent Number: 4,478,914
[45] Date of Patent: * Oct. 23, 1984

[54] PROCESS FOR APPLYING MULTIPLE LAYERS OF A PROTEIN AND A LIGAND EXTENDER TO A SURFACE AND TO THE MULTIPLE-LAYER SYSTEM

[76] Inventor: Roger W. Giese, 56 Oakland Ave., Quincy, Mass. 02170

[*] Notice: The portion of the term of this patent subsequent to Aug. 4, 1998 has been disclaimed.

[21] Appl. No.: 532,036

[22] Filed: Sep. 14, 1983

Related U.S. Application Data

[63] Continuation of Ser. No. 272,297, Jun. 10, 1981, abandoned, which is a continuation-in-part of Ser. No. 114,898, Jan. 24, 1980, Pat. No. 4,282,287.

[51] Int. Cl.³ .......................... B32B 5/16; B32B 9/00
[52] U.S. Cl. ........................................ 428/407; 427/2; 427/214; 427/220; 427/222; 427/331; 427/399; 427/400; 427/414; 428/403; 428/478.2
[58] Field of Search .................... 427/414, 400, 2, 399, 427/331, 299, 222, 214, 220; 428/15, 403, 407, 426, 473, 478.2

[56] References Cited

U.S. PATENT DOCUMENTS

| | | | |
|---|---|---|---|
| 4,132,528 | 1/1979 | Eikenberry et al. | 422/57 |
| 4,134,792 | 1/1979 | Boguslaski et al. | 435/7 |
| 4,168,300 | 9/1979 | Andersson et al. | 424/12 |
| 4,282,287 | 8/1981 | Giese | 427/2 |

OTHER PUBLICATIONS

Heitzmann et al., "Use of the Avidin-Biotin Complex for Specific Staining of Biological Membranes . . . " Proc., Nat. Sci., vol. 71, No. 9, pp. 3537-3541, Sep. 1974.
Bayer et al., "Affinity Cytochemistry: The Localization of Lectin and Antibody Receptors on Erythrocytes Via the Avidin-Biotin Complex" FEBS Letters, pp. 240-244, vol. 68, No. 2, Oct. 1976.
Bayer et al., "The Avidin-Biotin Complex as a Tool in Molecular Biology" Trends in Biochemical Science 3, N257, Nov. 1978.
Costello et al., "Enhancement of Immune Cellular Agglutination by Use of an Avidin-Biotin System", Clinical Chem., vol. 25, No. 9, 1979.
Jasiewicz et al., "Selective Retrieval of Biotin Labeled Cells Using Immobilized Avidin", Experimental Cell Research 100 (1976).
Bendor, Reunion de La Societe Francaise D'Immunologie, May, 1979.
Guesdon et al., "The Use of Avidin-Biotin Interaction in Immunoenzymatic Techniques", J. of Histochem. & Cytochem., vol. 27, pp. 1131-1139, 1979.
Guesdon et al., "Sensitive Titration of Antibodies and Antigens Using Erytho-Immunoassay," Ann. Immunol. 131C, pp. 389-396, 1980.

*Primary Examiner*—S. L. Childs
*Attorney, Agent, or Firm*—Richard P. Crowley

[57] ABSTRACT

A multiple-layer process for applying, in alternate, successive molecular layers, a protein material, and a ligand extender material to a surface to modify the properties of the surface and to the multiple-layer product so prepared.

29 Claims, 2 Drawing Figures

LAYERED SURFACE

PROCESS FOR APPLYING MULTIPLE LAYERS OF A PROTEIN AND A LIGAND EXTENDER TO A SURFACE AND TO THE MULTIPLE-LAYER SYSTEM

REFERENCE TO PRIOR APPLICATIONS

This is a continuation of application Ser. No. 272,297, filed June 10, 1981, now abandoned, which is a continuation-in-part application of Ser. No. 114,898, filed Jan. 24, 1980, now U.S. Pat. No. 4,282,287 issued Aug. 4, 1981.

BACKGROUND OF THE INVENTION

Avidin is a protein found in egg whites and contains four subunits. Biotin is a stable, water-soluble vitamin. Biotin and avidin interact specifically under mild and certain harsh conditions to form a strong, stable, avidin-biotin complex in which each of the four subunits of avidin bind a biotin molecule. This binding persists when biotin is attached by means of its carboxyl group to another molecule, or when avidin is attached to another molecule. For example, biotin may be secured or attached to molecules on the surface of a cell or to anticellular antibodies which have been reacted onto a cell, and then subsequently is reacted with a ferritin-avidin conjugate, to provide a method for localization studies in affinity cytochemistry (see, for example, *Trends in Biochemical Science*, 3, N257 (1978), hereby incorporated by reference). Biotinyl-antibody and conjugated avidin products (with fluorescein, rhodamine, ferritin or horse radish peroxidase) are offered commercially, to provide investigators with reagents for studying biochemical and immunochemical structures or processes; for example, the location or extent of a cell-surface substances.

A modified avidin-biotin system has been employed to enhance immune cellular agglutination of erythrocytes (see *Clinical Chemistry*, 25, No. 9, 1572 (1979), hereby incorporated by reference. Biotin or caproylamidobiotin was either attached directly to the cells or indirectly using biotin or caproylamidobiotin-anticellular antibody. The addition of avidin then achieved agglutination, and a biotin or caproylamidobiotin-conjugated macromolecule was added as an extender in conjunction with more avidin, to enhance the agglutination.

SUMMARY OF THE INVENTION

My invention relates to a process of preparing multiple layer system ("layering") and to the multiple layer system so prepared. In particular, my invention concerns a process of preparing a multiple-layer system involving repetitive, specific, molecular or particulate layers of a proteinaceous material and ligand material, to the multiple-layer system so prepared, and to the use of the system and process to change or modify surface properties.

My multiple-layer process and multiple-layer product comprise a protein such as avidin and a ligand material such as biotin (and any derivatives, analogs or substitutes of these which still comprise an analogous binding interaction) and a material referred to as an extender. An extender is defined as a molecule or substance to which one or more ligands such as biotin have been attached such that these ligands still undergo binding by the protein such as avidin. The extender useful in my invention may comprise those extenders which are described in the *Clinical Chemistry* publication, supra, or other biotin-modified molecules or particles. Typical and specific extenders include, but are not limited to: fibrinogen, albumin, succinylated polylysine and ribonuclease appropriately modified with biotin or biotin derivatives. These extenders may be used separately or in combination or as separate layers of different extenders as desired.

Typical examples of avidin derivatives include, but are not limited to: succinyl avidin, ferritin avidin, enzyme avidin and cross-linked avidin. A typical example of an avidin analog is the bacterial biotin-binding protein, streptavidin, whose physical and chemical characteristics are similar to those of avidin. A typical example of an avidin substitute or other proteins is a ligand-binding substance with multiple ligand-binding sites, such as a lectin, antibody, protein A (purified or cell-bound), etc., in conjunction with an appropriate ligand (lectins bind sugar ligands, antibodies bind hapten or antigenic determinant ligands, and protein A binds $F_c$ ligand). Typical examples of biotin derivatives as ligands include, but are not limited to: caproylamidobiotin and biocytin. Typical examples of biotin analogs are desthiobiotin and biotin sulfone and of biotin substitutes are ligands for appropriate substitute binding substances; that is, sugars, haptens or antigenic determinants, $F_c$, for lectins, antibodies, protein A, etc., as defined above.

The multiple-layer process is defined as the successive, repetitive attachment of the protein and extenders to a surface to build up alternate layers of each. The initial step could be attachment of either one of these reagents (covalently or non-covalently) to a surface, or direct firm attachment of biotins to the surface. For example, where the surface is, firstly, covalently bonded with biotin, then layering would be achieved by repetition of the following sequence of steps (a–d) to build up successive layers of avidin and extender: (a) add avidin; (b) wash away unbound avidin; (c) add extender; and (d) wash away unbound extender, and then, optionally, perform a derivatization reaction; for example, cross-linking or modifying of functional groups, in between any of the above steps and/or after all the layers have been developed to change the properties further; for example, provide a more complete coverage of the surface, more stability, different functional groups, etc. In my layering process, primarily or exclusively monomolecular or monoparticulate layers of avidin and extender (a single extender or various extender materials may be used in a given multiple-layer process) are built up on a surface, but the process may be relaxed by omitting washing steps, thereby possibly mixing in coverage with multimolecular or multiparticulate species.

Any conceivable surface may be employed, whether biological, nonbiological, organic, inorganic, or a combination of any of these, and whether formulated or existing as molecules, molecular aggregates, particles, strands, precipitates, gels, sheets, tubing, spheres, containers, capillaries, pads, slices, film, etc. (for example, cells, tissue, tumors, organelles, proteins, polymers, elastomers, microorganisms, viruses, nucleic acids, plastics, resins, polysaccharides, silica or silica-based materials, carbon, metals, inorganic salts, chromatographic supports, tests tubes, etc.); provided only that some component of the layering system can be attached firmly to initiate the process. The attachment of avidin to biotin or extender can proceed under mild conditions (for example, aqueous solvents and room temperature).

The basic concept of developing repetitive, specific, alternate, monomolecular or monoparticulate layers on a surface is unprecedented. My "layering" system bears no relation to conventional surface-treatment processes, such as painting, because of the latter's gross numbers of molecules and variable layer thickness involved, the poorly controlled nonspecific nature of the process, the complex and often crude nature of many of the components and the major effect achieved by the first or second layer with subsequent layers typically leading to equivalent or diminished returns.

My "layering" process constitutes a new process at the molecular or monoparticulate level, with an opportunity to develop specifically and to control molecular distances and constructions, with exact choices of components. In my process, the first layer is merely a beginning, and the overall layering process involves a careful and well-defined building up and constructing of an array of molecules or particles on a given surface in an exact and sophisticated manner, and with great variety, if so desired. The process and product are characterized by a unique array of characteristics which requires all of the aspects mentioned (repetitive, specific, alternate monomolecular or monoparticulate layers), and which qualitatively and/or quantitatively can differ vastly from the properties or effects achieved by the initial layer or even initial several layers.

Overall my layering avidin-biotin system offers significant advantages in terms of the overall accessibility, stability, cost, size, solubility and multiple binding sites of its components, and the analogs, derivatives and substitutes for avidin and biotin are within the scope of my layering system.

A wide variety of problems associated with surfaces are now subject to a new mode of attack with my multiple-layer process and product. For example, my process may be used to change the adsorptive, functional, catalytic, reactivity, transport, adhesive, stability, charge, toxicity, biological foreignness, frictional, electrical potential, chromatographic, pore size, rigidity, wettability, reflective, conductance, energy transfer, immunogenic, roughness, hardness, etc. properties of a surface; to stabilize the inherent properties of a surface; to determine distances between sites (for example, once the distance is layered, it is shut off from further layering, or signal molecules, such as a fluorescence molecule and a fluorescence quencher, or interacting spin labels, could be used to reveal when the layers from the sites reach a certain proximity); to establish connections between sites on the same or different surfaces; to cause movement of sites on or between surfaces and, therefore, of the surfaces themselves; to disrupt a surface; to provide an exact distance between functional molecules or substances on a surface or between different surfaces; to create, study, optimize or otherwise change an interaction or binding or disruption between surfaces or between surfaces and some other substances or molecules; to provide a special microenvironment or access or protection, etc. for functional molecules or substances on surfaces; to allow larger or more complex particles to be developed by starting with a core molecule or particle and building up layers; and to allow the development of exceedingly small circuitry.

Specific examples of some uses would be to increase the extent of attachment of an enzyme, antibody, coenzyme, fluorophor, radionuclide, drug or other special atom or molecule to a surface for enhancing immunoassay, affinity chromatography, therapy, enzyme engineering, solar-energy conversion, catalysis, etc.; to reduce the pore sizes of a dialysis or filtration surface; to change retention characteristics; to change the pore size and/or surface properties of silica or silica-based particles for chromatographic or adsorption-control purposes; to exert or to enhance a physical, chemical or biological activating, inhibiting, disrupting, toxicity or killing action against a desirable or undesirable surface, such as a tumor cell, infectious microorganism, diseased tissue or disease-causing agent; to change the foreignness (for example, immunogenicity) of host tissue for reduced rejection by donor or decreased graft-vs.-host response in tissue-transplant procedures; to reduce or eliminate the foreignness of artificial tissue or implant materials (for example, reduced thrombogenic action, reduced immune or phagocytic response) in artificial-organ or -tissue operations (for example, involving plastics and other polymers, etc.); to constitute a glue or adhesive for joining tissues to other tissues or artificial surfaces; to fix tissues; to preserve foods; to use in or achieve molecular surgery; to create channels or reservoirs for reactive molecules or products; to bring together drugs, enzymes, energy-transport molecules, etc. into an arrangement and structure which optimizes their performance and action; and to create novel physiological-transport agents. Other uses of my multiple-layer process and product would be apparent to a person skilled in the art.

My layering system will be demonstrated employing the process with certain caproylamidobiotin ribonuclease found particularly to be effective as an extender.

An appropriate model surface and signal extender are used to demonstrate my layering process. Essentially, nonadsorbing conditions for all reagents were achieved in order to avoid nonspecific effects. An aminoethylpolyacrylamide as a surface material and a signal extender were used; that is, horse radish peroxidase modified successively with hexanediamine/carbodiimide, caproylamidobiotin NHS and succinic anhydride.

My process includes not only the basic layering process, but also "amplification layering", to achieve relatively increasing amounts of corresponding substances in successive layers during this process. Such amplification layering is essential for many of the potential benefits and opportunities of layering to be realized fully. For example, a general, basic problem with surface treatments involving coatings of one to several molecules is that complete coverages are not achieved. An amplification-layering process can provide complete surface coverage, because of its ability to continue to expand the surface coating in all available directions.

For the purpose of illustration only, my multiple-layer process and product will be described with reference to certain specific embodiments; however, it is recognized that those persons skilled in the art may make certain changes and modifications, all within the scope and intent of my invention.

DESCRIPTION OF THE EMBODIMENTS

Figure 1:
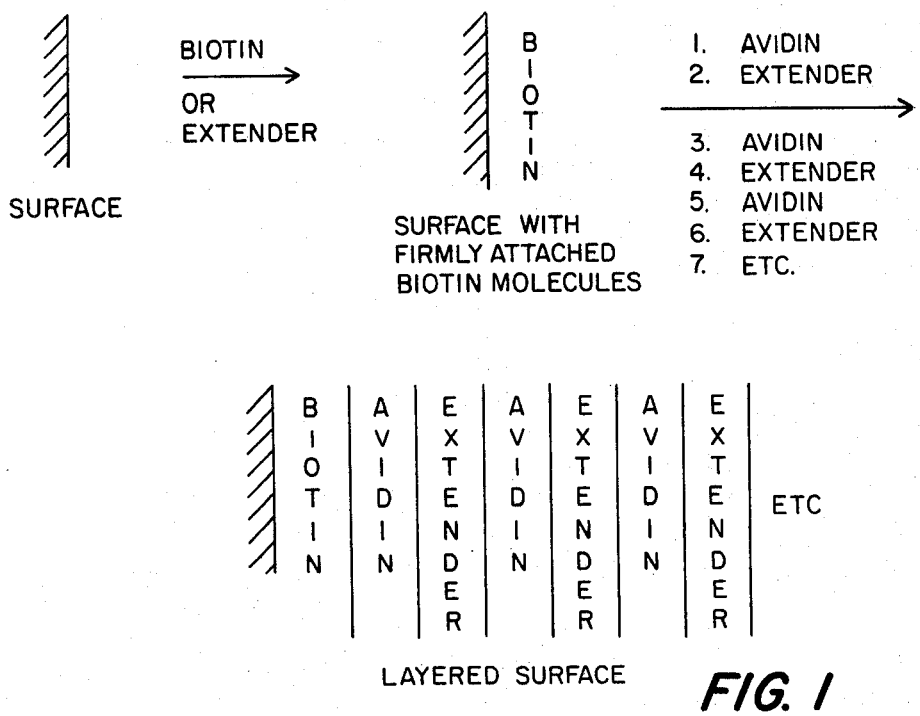
FIG. 1 is a schematic illustration of the multiple-layer process and layering system of my invention.

FIG. 1 is a schematic illustration of a multiple-layer process and layering system of my invention, wherein the biotin is covalently bonded directly to the illustrative surface in the first step, avidin is applied in the next step, and extender (a material to which biotin groups are attached as defined previously) is added, followed by repetitive further additions of avidin and noncovalent extender with intermediate washing steps to remove excess reagents.

It is recognized that the layers may be mixed, that various extenders and forms of avidin (and any derivatives, analogs or substitutes of these) may be used separately, concurrently, intermittently, etc. in a given layering process, that the layering process may result in constant, increasing or decreasing amounts of corresponding substances in successive layers, and that the layers may proceed in the form of molecular and/or particulate sheets, clumps, spheres, patches, rods, tubes, etc. from the initiation sites on the surface.

Figure 2:
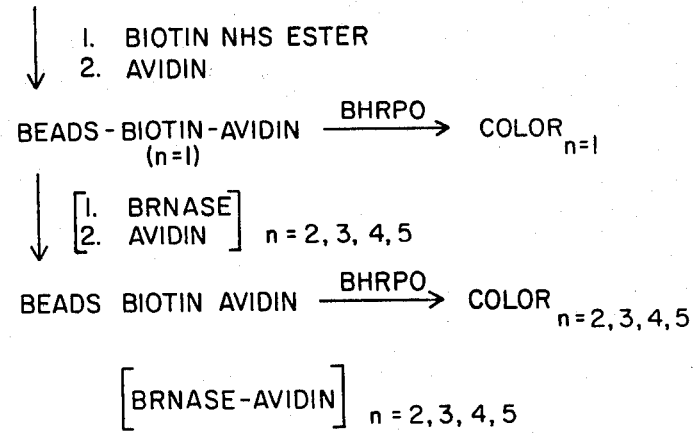
FIG. 2 is a schematic illustration of a specific multiple-layer process and layering system of my invention.

FIG. 2 shows a schematic illustration of a specific, multiple-layer process and product, wherein the surface comprises polyacrylamide particles containing reactive alkylamine groups, which then was modified by reaction with a layer of biotin-NHS esters. The modified surface was then coated with alternating successive layers of avidin and a biotin-ribonuclease extender material, illustrated as five successive layers, to modify the surface of the particles. The extent of avidin attachment in each layering step was monitored by adding an aliquot of biotin-horse radish peroxidase (BHRPO) to each avidin layer treatment. The BHRPO served as a signal extender. Appropriate washing and control steps and treatment were carried out. The HRPO color at 500 nanometers was measured after each avidin layering step as a measure of the amount of avidin (most specifically, available avidin-binding sites for BHRPO), and the layering process was found to generate increasing amounts of avidin with each avidin layer (amplification layering), one of the three possibilities (constant, decreasing or increasing) cited earlier. The color-vs.-number-of-layers data is as shown in Table I.

TABLE I

Absorbance 500 nm (color) vs. Number of Layering Cycles

| No. of Layers Avidin (n) | Color Absorbance | Absorbance Difference Values |
|---|---|---|
| 1 | .746 | .086* |
| 2 | .832 | .132 |
| 3 | .964 | .160 |
| 4 | 1.124 | .255 |
| 5 | 1.379 | |

*0.832 − 0.746 = 0.086

In order to illustrate more fully the nature of the invention and the manner of practicing the same, the following Example is presented:

EXAMPLE I

Materials

1. Affigel-701 from Bio-Rad—an aminoethyl derivative of polyacrylamide in a bead form, 1-3 microns in diameter. The beads were provided in an aqueous suspension at 25±3 μ/mol of amine groups/ml.
2. Phosphate buffered saline (PBS)—an 0.01M sodium phosphate, 0.15M sodium chloride, pH 7.4.
3. Avidin—dissolved in PBS at 0.1 mg/ml based on weight.
4. Wash buffer—The buffer used for all washing steps was PBS containing bovine serum albumin (BSA) at 0.02% wt and Tween-20 surfactant at 0.05% wt.
5. HRPO substrate—was freshly prepared by dissolving phenol (100 mg) and 4-aminoantipyrine (16.2 mg) in a solution composed of 0.5M $Na_2HPO_4$(2 ml), 0.5M $KH_2PO_4$(18 ml), water (180 ml) and 30% $H_2O_2$(20 μl).
6. Silanized glass tubes—Disposable borosilicate glass tubes (12×75 mm) were silanized by filling with a 2% solution of chlorotrimethylsilane in benzene. The silanizing reagent was decanted after ½ hour, the tubes rinsed with acetone and air-dried.
7. Biotin NHS ester (biotin N-hydroxysuccinimide ester)—was prepared as defined in Jasiewicz, M. M., Schoenberg, D. R., and Mueller, G. C., *Exp. Cell Res.* 100, 213 (1978), hereby incorporated by reference.
8. Caproylamidobiotin-NHS Ester and caproylamidobiotin-RNase (BRNase)—were prepared as defined previously (Costello, S. M., Felix, R. T. and Giese, R. W., *Clin. Chem.* 25, 1572 (1979), herein incorporated by reference).
9. BHRPO horse radish peroxidase (Worthington Biochemical)—10 mg were dissolved in 1 ml of water. This was added to a solution consisting of 1,6-hexanediamine (116 mg), 0.2M sodium pyrophosphate (2.0 ml), water (5.0 ml) and sufficient concentrated HCl to bring the pH to 5.5. A solid water-soluble carbodiimide, 1-ethyl-3-(3-dimethylaminopropyl) carbodiimide (EDC) was added to the gently mixed solution at room temperature. Three separate additions of 190 mg each were made over a 1-hour period. 1½ hours after the first addition, the contents of the beaker were placed in a dialysis bag and dialyzed against 4×400 ml of PBS (pH=7.4). An aliquot (10 ml) from the dialysis bag was added to a solution of caproylamidobiotin-NHS ester (4.1 mg) in N,N-dimethylformamide (DMF) (0.1 ml). This solution was allowed to stand at room temperature for 1½ hours and was then dialyzed against 4×400 ml of PBS (pH=7.4).

An aliquot (2 ml) of the above was placed in a dialysis bag and dialyzed against $NaHCO_3$ (1M) for 24 hours. The sample (at pH=8.6) was removed from the bag, placed in a small beaker with a magnetic mixer and reacted with 5×10 μl aliquots (15 minutes apart) of succinic anhydride (40 mg) in DMF (1 ml). The sample was placed in a dialysis bag 15 minutes after the last addition and dialyzed against 4×400 ml of PBS (pH=7.4).

Assuming 100% recovery of enzyme, the concentration of biotinyl-HRPO (BHRPO) would be approximately 0.8 mg/ml. It migrated electrophoretically (cellulose acetate, pH 8.6 buffer) in a manner similar to native enzyme (although the band was more diffuse).

10. Biotin-beads suspension—Affigel-701 (5.0 ml, about 125 μmol of amine groups) was added to PBS (5.0 ml). This suspension was vortexed 10 seconds, and biotin NHS ester (43 mg, 125 μmol) dissolved in DMF (0.1 ml) was added all at once. The reaction mixture was allowed to mix end over end for 2 hours at room temperature.

The beads were packed by centrifugation and the supernatant discarded. The bead pellet was resuspended in PBS and washed with 4×20 ml of PBS. The beads (biotin beads) were finally suspended in PBS (20 ml) containing NaN$_3$ (0.02%).

Layering of Biotin Beads

Aliquots (50 μl) of biotin-bead suspension (magnetically mixing) were placed in 12×75 mm silanized glass tubes. Each tubes was treated with avidin (0.1 mg in 1 ml PBS) for 10 minutes at room temperature. The beads were then centrifuged and the supernatants collected. The beads were washed ×3 with wash buffer.

A layer was applied to the avidin-biotin beads by suspending them in 1 ml of caproylamidobiotin RNase (BRNase approximately 60 μg/ml) for 10 minutes. The beads were then spun and the supernatants collected. The beads were then washed ×3 with wash buffer. The newly added biotin residues were next reacted with avidin as above. The sequence of avidin followed by BRNase, with intermittent washing steps, was repeated four more times. This process is set forth in FIG. 2.

Functional biotin binding sites on avidin-biotin beads (or layered beads) were detected by suspending aliquots of the beads after each avidin step in 200 μl of BHRPO (2 μg/ml) in PBS for 30 minutes. Unbound enzyme was removed by threefold washing with wash buffer. Bound enzyme was detected by addition of HRPO substrate (4.5 ml). After 30 minutes at room temperature, the tubes were chilled in an ice bath for 5 minutes and then spun. The supernatants were decanted and diluted with PBS (4.5 ml).

The $A_{500}$ values of the diluted substrate solutions were measured on a Gilford 240 using water as a reference, and are given in Table I. As seen, the amount of functional enzyme on the beads is greater with each cycle of layering, and the rate of increase (given by the difference values) also is increasing significantly as the layering proceeds; for example, the value 0.255 between layers 4 and 5 is 2.96 times greater than the value 0.086 between layers 1 and 2. This demonstrates the usefulness of layering for placing functional enzyme on a surface, increasing the amount of functional enzyme on a surface, and achieving an increasing rate of layering for the enzyme; that is, a relative increase in the amount of enzyme attached with each successive layer.

Avidin and some of the ligand binding proteins which may be employed in the practice of my invention are set forth in Table II.

TABLE II

Avidin and Some Other Ligand-binding Proteins

| Protein | Ligand | Affinity (Ka) | Usual No. of binding sites |
|---|---|---|---|
| Lectins | Simple sugars membrane sites | $10^3$–$10^4$ $10^6$–$10^7$ | 4 |
| Protein A (S. aureus) | $F_c$ of IgG | $10^7$ | 4 |
| Antibodies | Haptens | $10^5$–$10^{11}$ | 2 |
| | Antigenic determinants | $10^5$–$10^{11}$ | 2 |
| Avidin | Biotin | $10^{15}$ | 4 |
| Streptavidin | Biotin | — | 4 |

EXAMPLE II

Lectin layering of Affigel-701 beads

Materials
1. The Affigel-701, PBS, wash buffer, HRPO substrate, silanized glass tubes, aminohexyl-HRPO, and RNase are the same as cited in Example I (Layering of Biotin Beads). Concanavalin A, a mannose-binding lectin, is purchased from Sigma Chem. Co.
2. α-D-Mannose hydrazide is prepared as defined in G. A. Orr and R. R. Rando, *NATURE*, 1978, 272, 722–725, herein incorporated by reference.
3. α-D-Mannose residues are attached to the Affigel-701 beads, aminohexyl-HRPO, and RNase by the same procedure except that the beads are washed free of excess reagents with intermittent centrifugation, whereas dialysis is used for the two proteins. The amino groups on Affigel 701, aminohexyl-HRPO, and RNase are first reacted with aqueous glucose in the presence of sodium borohydride. After removal of excess reagents, aqueous periodic acid oxidation of the attached glucose residues yields aldehydes to which α-D-mannose hydrazide residues are attached by reaction in the presence of sodium borohydride. This affords mannosyl-Affigel-701, mannosyl-HRPO, and mannosyl-RNase, respectively. As before, excess reagents are removed by centrifugation in the case of the Affigel, and by dialysis in the case of mannosyl-HRPO and mannosyl-RNase.

Layering of Mannosyl-Affigel-701 Beads

This layering experiment is conducted the same as in Example I, except that concanavalin A is substituted for avidin, mannosyl-Affigel-701 for biotin beads, mannosyl-HRPO for BHRPO, and mannosyl-RNase for BRNase.

EXAMPLE III

Layering of *Staphylococcal aureus* cells involving Protein A and IgG

Materials
1. PBS is defined in Example I.
2. SA cells (*staphylococcal aureus* cells) are commercially available, e.g. from The Enzyme Center, Boston, MA, as "IgGsorb". SA cells contain a large number of protein A molecules on their surfaces; protein A binds to $F_c$ on many types of IgG molecules.
3. Oligomeric IgG (IgG dimers, trimers, etc.) is prepared by reacting dilute, aqueous IgG (e.g. Sigma Chem. Co.) with 1-ethyl-3-(3-dimethylaminopropyl)-carbodimide, then dialyzing the product against PBS, and removing any precipitate by centrifugation.
4. FITC—Protein A is a protein A conjugated with fluoresceneisothiocyanate. This fluorescent molecule is commercially available from Pharmacia Fine Chemicals.
5. Oligomeric protein A is prepared by the same procedure as for oligomeric IgG, except starting with protein A, which is commercially available, e.g. from Pharmacia Fine Chemicals.

Layering of SA Cells
1. The SA cells are suspended in PBS and treated with oligomeric IgG.
2. The SA cells, now coated with oligomeric IgG, are centrifuged, the oligomeric IgG supernatant is removed and saved, and the coated SA cells are washed with PBS and isolated by centrifugation.
3. The IgG coated SA cells are then reacted with one of the following: further SA cells, oligomeric protein A, Protein A, or FITC-protein A.
4. The layered SA cells are washed as before, coated again with oligomeric IgG and washed as before.
5. The sequence of steps 3 and 4 is repeated as many times as desired, generating SA cells which are layered with alternate coatings involving protein A and IgG. The extent of layering can be monitored conveniently whenever FITC-Protein A is reacted onto the IgG-coated surface, since FITC-protein A is fluorescent.

EXAMPLE IV

Antibody Layering of Affigel-701 Beads

Materials
1. The Affigel-701, PBS, wash buffer, HRPO substrate, silanized glass tubes, aminohexyl-HRPO, and RNase are the same as cited in example I (layering of biotin beads).
2. Fluorodinitrobenzene, dissolved in ethanol, is reacted in aqueous, sodium carbonate buffer with the amino groups on Affigel-701, aminohexyl-HRPO, and RNase, yielding the following DNP (dinitrophenyl) products, respectively: DNP-Affigel-701, DNP-aminohexyl-HRPO, and DNP-RNase. Excess fluorodinitrobenzene and its hydrolysis products are removed from the DNP-Affigel-701 by centrifugation and washing, and from the DNP-aminohexyl-HRPO and DNP-RNase by dialysis.
3. Anti-DNP antibody is available commercially from Miles Biochemicals. Monoclonal anti-DNP antibody may also be developed by hybridoma techniques and utilized.

Layering of DNP-Affigel 701 beads

This layering experiment is conducted the same as in example I, except that anti-DNP antibody is substituted for avidin, DNP-Affigel-701 for biotin beads, DNP-HRPO for BHRPO, and DNP-RNase for BRNASE.

EXAMPLE V

Avidin Layering of Glass Test Tubes

Materials
1. The materials are the same as in example I, except that biotinyl-aminopropyl-glass test tubes are used in place of the two components, biotin beads and silanized glass tubes.
2. Biotinyl-aminopropyl-glass test tubes are prepared as follows: first the test tubes are reacted with γ-aminopropyltriethoxysilane in toluene as described by H. H. Weetall and A. M. Filbert (1974) in *Methods in Enzymology* (W. B. Jakoby and M. Wilchek, eds.) 34, p. 59 herein incorporated by reference; then the amino groups on the glass surface are reacted with biotin-NHS dissolved in acetonitrile.

Layering of glass tubes

The procedure is the same as in example 1 except that no beads are involved, and the centrifugation steps are omitted. Thus, the first step is to treat the test tubes with avidin (0.1 mg in 1 ml PBS) for 10 min at room temperature. The avidin solution is poured out and saved. The test tubes are washed ×3 with wash buffer, and treated for 10 min with BRNase. This solution is poured out and saved. The test tubes are washed ×3 with wash buffer, the newly added biotin residues are reacted as before with avidin, and so on, according to the steps in example I. As before, at any step when the last layer is avidin, the amount of reactive biotin on the surface can be determined by reacting the tubes with BHRPO, and then, after washing, determining the bound enzyme by added HRPO substrate.

EXAMPLE VI

Avidin Layering of Fibrinogen

Materials

The materials are the same as in Example I, except that Fib-B (biotinated fibrinogen, which is prepared as described by S. M. Costello, R. T. Felix, and R. W. Giese, Clin. Chem. 25 (1979), p. 1572, previously incorporated by reference) replaces the biotin beads.

Layering the Fib-B

The procedure is the same as in Example I, except that Fib-B replaces the biotin beads, and that excess reagents are removed from Fib-B after each layering step by means of, e.g., gel filtration in wash buffer on Sephadex G-100 or with an ultrafiltration membrane (e.g. from Millipore or Amicon) rather than by centrifugation and washing. In the case of the Sephadex G-100 column, the layered Fib-B elutes first from this column, and is concentrated by precipitation with organic solvent, or by lyophilization, as necessary, before the next step.

EXAMPLE VII

Avidin Layering of Dialysis Tubing

Materials
1. Cellulosic dialysis membrane is commercially available, e.g. from VWR.
2. Av-membrane is prepared by reacting the cellulosic dialysis membrane with CNBr dissolved in aqueous sodium carbonate. After a short reaction period (e.g. 5 to 10 min), the activated membrane is washed with PBS and reacted with a solution of avidin in PBS.
3. All other materials are the same as cited in Example I.

Layering of dialysis tubing
1. The Av-membrane is treated with B-RNase dissolved in PBS, and then washed ×3 with wash buffer.
2. This B-RNase-coated membrane is treated with avidin in PBS, and then washed ×3 with wash buffer, to yield a layer of avidin.
3. Steps 1 and 2 can be repeated in sequence until the desired smaller pore size or other characteristics of the membrane are achieved.

Having thus described my invention, what I claim is:

1. A process of modifying the surface properties of a material, which process comprises: applying alternate, molecular, successive layers of first and second materials to the surface to be modified, the first material comprising a ligand binding proteinaceous material and the second material comprising a reactive ligand extender material, one of the materials reacted to the surface and, thereafter, at least one additional layer of the first and second materials alternately secured and noncovalently ligand reacted to the underlying layer of the other material, to provide a modified surface, with the first or second material as the top surface layer.

2. The process of claim 1 wherein the proteinaceous first material is selected from the group consisting of lectins, protein A, avidin derivatives, avidin, streptavidin, antibodies and combinations thereof.

3. The process of claim 1 wherein the ligand second material is selected from the group consisting of simple sugars, biotin, biotin derivatives, biotin analogs, $F_c$ fragments of an immunoglobulin, hapten and combinations thereof.

4. The process of claim 3 wherein the ligand second material includes a dinitrophenyl group.

5. The process of claim 1 wherein the proteinaceous first material comprises protein A conjugated with a fluorescent group.

6. The process of claim 1 wherein the material whose surface is to be modified, is selected from the group of materials consisting of polymeric materials containing at least one amino group, amino silanized glass, fibrinogen, a cellulosic dialysis membrane silica, proteins, nucleic acids, and *staphylococcal aureus* cells.

7. The process of claim 1 wherein the material whose surface properties are to be modified comprises an amino polyacrylamide polymer.

8. The process of claim 1 wherein the proteinaceous first material comprises concanavalin A, the second material comprises mannose, and the material whose surface is to be modified comprises an amino polymer.

9. The process of claim 1 wherein the proteinaceous first material comprises protein A, the second ligand material comprises antibodies, and the material whose surface is to be modified comprises *staphylococcal aureus* cells.

10. The process of claim 1 wherein the proteinaceous first material comprises antibodies, the second material comprising a dinitrophenyl group.

11. The process of claim 1 wherein the top surface of the process comprises the second ligand extender material.

12. The process of claim 1 which includes pretreating the surface with a monomolecular layer of biotin, and wherein the first proteinaceous material is applied over and secured to the biotin layer.

13. The process of claim 1 which includes:
 (a) applying a monomolecular layer of an organic ligand second material and covalently binding the second material to the surface;
 (b) applying and reacting a monomolecular layer of the ligand-binding proteinaceous material to the first layer; and noncovalently
 (c) applying and noncovalently reacting a monomolecular layer of a ligand extender material to the proteinaceous material layer.

14. The process of claim 1, which process includes varying the concentration of the first or second material in the alternate, successive layers.

15. The process of claim 14 which includes increasing the concentration of the alternate, successive layers of the first and second materials.

16. The process of claim 14 which includes decreasing the concentration of the alternate, successive layers of the first and second materials.

17. The process of claim 1 which includes applying alternate, successive layers of approximately the same stochiometric concentration.

18. The process of claim 1 wherein the surface comprises a polymeric surface.

19. The process of claim 18 wherein the surface comprises the surface of finely-divided, polyacrylamide, polymer particles.

20. The process of claim 18 wherein the surface to be modified comprises erythrocytes.

21. The process of claim 1 wherein the surface to be modified comprises the surface of amino-containing polymer, and the process comprises applying a layer of ligand-NHS esters to the surface of the particles, and, thereafter, applying successive, alternate, monomolecular layers of proteinaceous material and ligand-ribonuclease material.

22. The process of claim 1 wherein the first and second materials comprise monomolecular layers and wherein the second extender material is selected from the groups consisting of biotin-NHS, caproylamidobiotin NHS, caproylamidobiotin ribobuclease, and caproylamidobiotin-horse radish peroxidase.

23. The process of claim 1 which includes reacting at least one of the proteinaceous layers with a ligand-horse radish peroxidase or a ligand ribonuclease as a signal extender.

24. The layering system produced by the process of claim 1.

25. A process of modifying the surface properties of a material, which process comprises:
 (a) applying alternate successive layers of a first or second material to the surface to be modified, the proteinaceous first material selected from the group consisting of lectins, protein A, avidin, avidin derivatives, streptavidin, antibodies and combinations thereof, and the ligand second extender material selected from the group consisting of simple sugars, biotin, biotin derivatives, biotin analogs, $F_c$ fragments of an immunoglobulin, hapten and combinations thereof to provide at least two noncovalent successive layers;
 (b) washing the surface between each applying step to remove unreacted first or second material; and
 (c) recovering a multiple layer material whose surface is modified.

26. The process of claim 25 wherein the ligand second material comprises a ligand N-hydroxysuccinimide material.

27. The multiple layer system produced by the process of claim 25.

28. The process of claim 1 wherein each layer of the first and second material comprises a monomolecular or monoparticulate layer.

29. The multiple layer system produced by the process of claim 28.

* * * * *

REEXAMINATION CERTIFICATE (3226th)
United States Patent [19]
Giese

[11] B1 4,478,914
[45] Certificate Issued  *Jun. 17, 1997

[54] PROCESS FOR APPLYING MULTIPLE LAYERS OF A PROTEIN AND A LIGAND EXTENDER TO A SURFACE AND TO THE MULTIPLE LAYER SYSTEM

[76] Inventor: Roger W. Giese, 56 Oakland Ave., Quincy, Mass. 02170

Reexamination Request:
No. 90/003,847, May 11, 1995

Reexamination Certificate for:
Patent No.: 4,478,914
Issued: Oct. 23, 1984
Appl. No.: 532,036
Filed: Sep. 14, 1983

[ * ] Notice: The term of this patent shall not extend beyond the expiration date of Pat. No. 4,282,287.

Related U.S. Application Data

[63] Continuation of Ser. No. 272,297, Jun. 10, 1981, abandoned, which is a continuation-in-part of Ser. No. 114,898, Jan. 24, 1980, Pat. No. 4,282,287.

[51] Int. Cl.[6] .................. B32B 5/16; B32B 9/00
[52] U.S. Cl. .............. 428/407; 428/403; 428/478.2; 427/2.11; 427/2.13; 427/2.3; 427/214; 427/222; 427/220; 427/399; 427/400; 427/414; 427/331; 435/7.5; 435/177; 435/822; 435/827; 435/828; 435/969
[58] Field of Search .................. 427/2.11, 214, 427/222, 220, 399, 400, 414, 331, 2.13, 2.3; 428/403, 407, 478.2; 435/7.5, 177, 822, 827, 828, 969

[56] References Cited

U.S. PATENT DOCUMENTS

| | | | |
|---|---|---|---|
| 4,132,528 | 1/1979 | Eikenberry et al. | 422/57 |
| 4,134,792 | 1/1979 | Boguslaski et al. | 435/7 |
| 4,168,300 | 4/1979 | Andersson et al. | 424/12 |
| 4,282,287 | 8/1981 | Giese | 427/2 |
| 4,298,685 | 11/1987 | Parikh et al. | 435/7 |

OTHER PUBLICATIONS

Heitzmann et al., "Use of the Avidin–Biotin Complex for Specific Staining of Biological Membranes...", Proc., Nat. Sci., vol. 71, No. 9, pp. 3537–3541, Sep. 1974.

Bayer et al., "Affinity Cytochemistry: The Localization of Lectin and Antibody Receptors on Erythrocytes Via the Avidin–Biotin Complex" FEBS Letters, pp. 240–244, vol. 68, No. 2, Oct. 1976.

Bayer et al., "The Avidin–Biotin Complex as a Tool in Molecular Biology" Trends in Biochemical Science 3, N257, Nov. 1978.

Guesdon et al., "The Use of Avidin–Biotin Interaction in Immunoenzymatic Techniques", J. of Histochem. & Cytochem., vol. 27, pp. 1131–1139, 1979.

Jasiewicz et al., "Selective Retrieval of Biotin Labeled Cells Using Immobilized Avidin", Experimental Cell Research 100 (1976).

Bendor, Reunion de La Societe Francaise D'Immunologie, May, 1979.

Guesdon et al., "Sensitive Titration of Antibodies and Antigens Using Erytho–Immunoassay," Ann. Immunol. 131C, pp. 389–396, 1980.

Costello et al., Clin. Chem., vol. 25, No. 9, pp. 1572–1580, 1979.

"Hapten–Sandwich Labeling: II. Immunospecific Attachment of Cell Surface Markers Suitable for Scanning Electron Microscopy" by M.K. Nemanic, D.P. Carter, D.R. Pitelka, and L. Wofsy The Journal of Cell Biology vol. 64, pp. 311–321, 1975.

*Primary Examiner*—Chhaya D. Sayala

[57] ABSTRACT

A multiple-layer process for applying, in alternate, successive molecular layers, a protein material, and a ligand extender material to a surface to modify the properties of the surface and to the multiple-layer product so prepared.

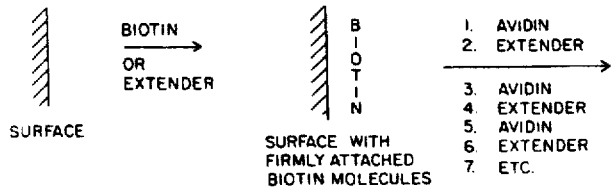

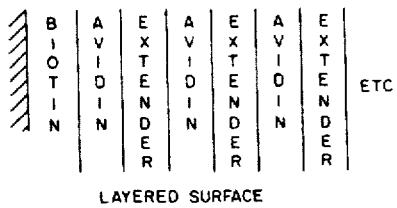

LAYERED SURFACE

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4, 10, 18 and 20 are cancelled.

Claims 1-3, 6, 11-13, 19, 21, 24-25 and 29 are determined to be patentable as amended.

Claims 5, 7-9, 14-17, 22-23, 26-28, dependent on an amended claim, are determined to be patentable.

New claims 30, 31, 32-56 and 57-73 are added and determined to be patentable.

1. A process of modifying the surface properties of a material, which process comprises: applying alternate, molecular, successive layers of first and second materials to the surface to be modified, the first material comprising a ligand binding proteinaceous material and the second material comprising a reactive ligand extender material, [one of the materials] *wherein a layer of the first material is* reacted to the surface and, thereafter, [at least one] additional [layer] *layers* of the first and second materials *are* alternately secured and noncovalently ligand reacted to the underlying layer [of the other material,] to provide a modified surface, with the first or second material as the top surface layer *and at least a layer sequence of a first material, a second material and a first material.*

2. The process of claim 1 wherein the proteinaceous first material is selected from the group consisting of lectins, protein A, avidin derivatives, avidin[,] *and* streptavidin[, antibodies and combinations thereof].

3. The process of claim 1 wherein the ligand second material is selected from the group consisting of [simple] sugars, biotin, biotin derivatives[,] *and* biotin analogs[, F_c fragments of an immunoglobin, hapten and combinations thereof].

6. The process of claim 1 wherein the material whose surface is to be modified, is selected from the group of materials consisting of [polymeric materials containing at least one amino group,] amino silanized glass, [fibrinogen, a] *silica, silica-based materials, biotinated fibrinogen,* cellulosic dialysis membrane [silica, proteins, nucleic acids, and staphylococcal aureus cells] *and polymers*.

11. The process of claim 1 wherein the top surface *layer* of the process comprises the [second ligand extender] *first* material.

12. The process of claim 1 which includes [pretreating] *treating* the surface with a monomolecular layer of biotin, and wherein the first proteinaceous material *is avidin and* is applied *as a first layer* over and secured to the biotin layer and thereafter applying successive layers of a second extender material and an avidin first material.

13. The process of claim [1] *25* which includes:
a) applying a monomolecular layer of an organic ligand second material and covalently binding the second material to the surface;
b) applying and reacting a monomolecular layer of the ligand-binding proteinaceous *first* material to the first layer; and [noncovalently]
c) applying and [noncovalently] *ligand* reacting a monomolecular layer of a ligand extender *second* material to the proteinaceous *first* material layer.

19. The process of claim [18] *1* wherein the surface comprises the surface of finely-divided, polyacrylamide, polymer particles.

21. The process of claim 1 wherein the surface to be modified comprises the surface of amino-containing polymer[, and the process comprises applying a layer of ligand NHS esters to the surface of the particles, and, thereafter, applying successive, alternate, monomolecular layers of proteinaceous material and ligand-ribonuclease material].

24. The layering [system] *product* produced by the process of claim 1.

25. A process of modifying the surface properties of a material, which process comprises:
a) applying alternate successive layers of a first [or] *and* second material to the surface to be modified, the proteinaceous, *ligand binding* first material selected from the group consisting of lectins, [protein A,] avidin, avidin derivatives, *and* streptavidin[, antibodies and combinations thereof, and the] *with a* ligand [second extender] *extender second* material selected from the group consisting of [simple] sugars, biotin, biotin derivatives, biotin analogs, F_c fragments of an immunoglobulin[, hapten] and combinations thereof to provide at least two noncovalent *ligand-connected* successive layers; *and*

[b) washing the surface between each applying step to remove unreacted first or second material; and]

[c)] *b)* recovering a multiple layer material whose surface is modified.

29. The multiple layer [system] *product* produced by the process of claim 28.

30. *The process of claim 1 which includes applying successive layers to the material to be modified starting with avidin, avidin derivative or streptavidin, and thereafter, at least one additional layer of avidin, avidin derivative or streptavidin and a layer of ligand extender material.*

31. *The process of claim 2 wherein the avidin derivative is selected from the group consisting of succinyl avidin, ferritin avidin, enzyme avidin and cross-linked avidin.*

32. *The process of claim 1 wherein the reactive ligand extender material is selected from the group consisting of biotin-modified particles and biotin-modified molecules used separately or in combination.*

33. *The process of claim 3 wherein the biotin analogs are selected from the group consisting of desthiobiotin and biotin sulfone.*

34. *The process of claim 3 wherein the biotin derivatives are selected from the group consisting of caproylamidobiotin and biocytin.*

35. *The process of claim 1 wherein the surface of the material to be modified is selected from the group consisting of particles, strands, molecules, aggregates, spheres, sheets, tubings, gels, containers, slices, films and pads.*

36. The process of claim 1 which includes employing a signal extender as the top surface layer.

37. The process of claim 1 which includes employing a signal extender to determine amounts of layering or available binding sites on the modified material surface.

38. The process of claim 37 wherein the signal extender is a protein fluorescent molecule.

39. The process of claim 37 wherein the signal extender is selected from the group consisting of biotinyl-horseradish peroxidase, dinitrophenyl horseradish peroxidase and mannosyl horseradish peroxidase.

40. The process of claim 37 wherein the signal extender is protein A conjugated with a fluoroesceneisothiocyanate fluorescent molecule.

41. The process of claim 1 which includes modifying the surface of the material by a reactive alkylamine group for reaction with the material first layered onto the surface.

42. The process of claim 1 wherein each additional, alternate, successive layer of first or second material is monomolecular or monoparticulate in thickness.

43. The process of claim 25 which includes applying a first layer to the surface to be modified of a first material, then applying a second layer of a second material, then applying a second layer of the first material to the second layer of the second material.

44. The process of claim 25 which includes applying successive layers to the material starting with avidin, avidin derivative or streptavidin, next applying a ligand extender material, and thereafter, applying at least one additional layer of avidin, avidin derivative or streptavidin.

45. The process of claim 25 which includes employing a signal extender to determine amounts of layering or available binding sites on the modified material surface.

46. The process of claim 45 wherein the signal extender comprises a protein fluorescent molecule.

47. The process of claim 46 wherein the signal extender is a fluorescent molecule.

48. The process of claim 46 wherein the signal extender is selected from the group consisting of biotin horseradish peroxidase and biotin ribonuclease.

49. The multiple layer product of claim 48.

50. The process of claim 25 wherein the extender material is caproylamidobiotin ribonuclease.

51. The process of claim 25 which includes forming a signal extender as the top surface layer.

52. The process of claim 25 wherein the surface of the material to be modified is selected from the group consisting of particles, strands, molecules, aggregates, spheres, sheets, tubings, gels, containers, slices, films and pads.

53. The process of claim 25 wherein the surface of the material to be modified comprises a cellular surface.

54. The process of claim 25 which includes washing the surface between applying successive layers of the first and second materials.

55. The process of claim 25 which includes applying a first layer to the surface to be modified of a second material, then applying a second layer of a first material, then applying a third layer comprising a second material to the second layer of the first material.

56. The process of claim 25 wherein the first and second materials comprise monolayers and wherein the second ligand extender material is prepared from the group consisting of biotin-NHS and caproylamidobiotin NHS.

57. The process of claim 25 which includes pretreating the surface of the material to be modified with a monomolecular layer of biotin and applying the first material over and secured to the biotin layer.

58. The process of claim 25 which includes varying the concentration of the first or second material in the alternate, successive layers.

59. The process of claim 25 which includes increasing the concentration of the alternate, successive layers of the first and second materials.

60. The process of claim 25 which includes decreasing the concentration of the alternate, successive layers of the first and second materials.

61. The process of claim 25 which includes applying alternate, successive layers of approximately the same stoichiometric concentration.

62. The process of claim 25 wherein the material whose surface properties are to be modified comprises an amino polymer.

63. The process of claim 25 wherein the proteinaceous first material comprises concanavalin A, the second material comprises mannose as a ligand, and the material whose surface is to be modified comprises an amino polymer.

64. The process of claim 25 wherein the avidin derivative is selected from the group consisting of succinyl avidin, ferritin avidin, enzyme avidin and cross-linked avidin.

65. The process of claim 25 wherein the reactive ligand extender material is selected from the group consisting of biotin-modified particles and biotin-modified molecules used separately or in combination.

66. The process of claim 25 wherein each additional alternate, successive layer of first or second material is monomolecular or monoparticulate in thickness.

67. The process of claim 25 which includes monitoring the extend of attachment of a first material by adding a signal extender to each layer or to the top layer.

68. The process of claim 25 which includes applying at least one layer comprising a mixture of a first and a second material as an applied layer.

69. The process of claim 25 which includes applying at least one layer composed of an avidin derivative or streptavidin as a first material with a biotin-modified enzyme as a second material.

70. The process of claim 25 which includes applying a layer of a second ligand material to the surface to be modified, which second ligand material is selected from the group consisting of sugars, biotin, biotin derivatives, and biotin analogs.

71. The process of claim 25 wherein the ligand extender second material comprises a biotin-conjugated protein material.

72. The process of claim 25 wherein the ligand extender second material comprises polylysine-biotin.

73. The process of claim 25 wherein the top surface of the process comprises the ligand binding proteinaceous first material.

* * * * *